(12) United States Patent
Kittelsen et al.

(10) Patent No.: US 6,553,996 B2
(45) Date of Patent: *Apr. 29, 2003

(54) DENTAL APPLIANCE WITH ANTIMICROBIAL ADDITIVE

(76) Inventors: Jon D. Kittelsen, 1511 Innsbruck Dr. North, Fridley, MN (US) 55432; Henry D. Cross, III, 546 Old Field Rd., Mt. Gilead, Murrell's Inlet, SC (US) 29576; Paul C. Belvedere, 5824 Creek Valley Rd., Edina, MN (US) 55439-1212; Mark Herman, 1400 Lincoln, Minneapolis, MN (US) 55403

( * ) Notice: Subject to any disclaimer, the term of this patent is extended or adjusted under 35 U.S.C. 154(b) by 0 days.

This patent is subject to a terminal disclaimer.

(21) Appl. No.: 09/828,111

(22) Filed: Apr. 6, 2001

(65) Prior Publication Data

US 2002/0066454 A1 Jun. 6, 2002

Related U.S. Application Data

(63) Continuation-in-part of application No. 09/658,102, filed on Sep. 8, 2000, now Pat. No. 6,257,239.

(51) Int. Cl.⁷ .................................................. A61C 5/14
(52) U.S. Cl. ........................ 128/859; 128/861; 128/862; 433/6
(58) Field of Search ................................ 128/846, 848, 128/859–862; 433/6; 602/902

(56) References Cited

U.S. PATENT DOCUMENTS

| | | |
|---|---|---|
| 257,038 A | 4/1882 | McMann |
| 1,117,928 A | 11/1914 | Thurmond |
| 1,323,832 A | 12/1919 | Chige |
| 1,461,209 A | 7/1923 | Bridges |
| 1,470,888 A | 10/1923 | Smedley |
| 1,487,392 A | 3/1924 | Lee |
| 2,118,980 A | 5/1938 | Montgomery et al. |
| 2,257,709 A | 9/1941 | Anderson |
| 2,423,005 A | 6/1947 | Chaiken |
| 2,630,117 A | 3/1953 | Coleman |
| 2,643,652 A | 6/1953 | Cathcart |
| 2,659,366 A | 11/1953 | Savarese |
| 2,669,988 A | 2/1954 | Carpenter |
| 2,678,043 A | 5/1954 | Stark |
| 2,694,397 A | 11/1954 | Herms |
| 2,702,032 A | 2/1955 | Freedland |
| 2,708,931 A | 5/1955 | Freedland |
| 2,750,941 A | 6/1956 | Cathcart |
| 2,833,278 A | 5/1958 | Ross |
| 2,847,003 A | 8/1958 | Helmer et al. |
| 2,933,811 A | 4/1960 | Lifton |
| 2,966,908 A | 1/1961 | Cathcart et al. |
| 3,016,052 A | 1/1962 | Zubren |
| 3,058,462 A | 10/1962 | Greenblum |

(List continued on next page.)

FOREIGN PATENT DOCUMENTS

| | | |
|---|---|---|
| CA | 1147583 | 6/1983 |
| DE | 480423 | 7/1929 |

OTHER PUBLICATIONS

Mouth Protectors: Give Your Teeth a Sporting Chance, American Dental Association, 1985.

(List continued on next page.)

*Primary Examiner*—Michael A. Brown
(74) *Attorney, Agent, or Firm*—Gerald E. Helget; Nelson R. Capes; Briggs and Morgan

(57) ABSTRACT

A dental appliance adapted to lie within the mouth of a person having occlusal posterior pads optionally with a connective arch or a u-shaped style base with upstanding labial and/or buccal walls. An antimicrobial additive is incorporated into the resin concentrate prior to molding of the dental appliance which will permit controlled migration from the appliance internal regions to the surface of the appliance.

6 Claims, 1 Drawing Sheet

U.S. PATENT DOCUMENTS

| | | |
|---|---|---|
| 3,073,300 A | 1/1963 | Berghash |
| 3,082,765 A | 3/1963 | Helmer |
| 3,107,667 A | 10/1963 | Moore |
| 3,124,129 A | 3/1964 | Grossberg |
| 3,126,002 A | 3/1964 | Owens |
| 3,203,417 A | 8/1965 | Helmer |
| 3,207,153 A | 9/1965 | Goldstein |
| 3,223,085 A | 12/1965 | Gores et al. |
| 3,247,844 A | 4/1966 | Berghash |
| 3,312,218 A | 4/1967 | Jacobs |
| 3,319,626 A | 5/1967 | Lindsay |
| 3,407,809 A | 10/1968 | Ross |
| 3,411,501 A | 11/1968 | Greenberg |
| 3,416,527 A | 12/1968 | Hoef |
| 3,448,738 A | 6/1969 | Berghash |
| 3,457,916 A | 7/1969 | Wolicki |
| 3,485,242 A | 12/1969 | Greenberg |
| 3,496,936 A | 2/1970 | Gores |
| 3,505,995 A | 4/1970 | Greenberg |
| 3,513,838 A | 5/1970 | Foderick et al. |
| 3,518,988 A | 7/1970 | Gores |
| 3,532,091 A | 10/1970 | Lerman |
| 3,682,164 A | 8/1972 | Miller |
| 3,692,025 A | 9/1972 | Greenberg |
| 3,768,465 A | 10/1973 | Helmer |
| 3,864,832 A | 2/1975 | Carlson |
| 3,916,527 A | 11/1975 | Linkow |
| 3,924,638 A | 12/1975 | Mann |
| 3,943,924 A | 3/1976 | Kallestad et al. |
| 4,030,493 A | 6/1977 | Walters et al. |
| 4,044,762 A | 8/1977 | Jacobs |
| 4,063,552 A | 12/1977 | Going et al. |
| 4,114,614 A | 9/1978 | Kesling |
| 4,185,817 A | 1/1980 | Peterson |
| 4,211,008 A | 7/1980 | Lerman |
| 4,330,272 A | 5/1982 | Bergersen |
| 4,337,765 A | 7/1982 | Zimmerman |
| 4,348,178 A | 9/1982 | Kurz |
| 4,376,628 A | 3/1983 | Aardse |
| 4,457,708 A | 7/1984 | Dufour |
| 4,490,112 A | 12/1984 | Tanaka et al. |
| 4,495,945 A | 1/1985 | Liegner |
| 4,519,386 A | 5/1985 | Sullivan |
| 4,568,280 A | 2/1986 | Ahlin |
| 4,591,341 A | 5/1986 | Andrews |
| 4,640,273 A | 2/1987 | Greene et al. |
| 4,671,766 A | 6/1987 | Norton |
| 4,672,959 A | 6/1987 | May et al. |
| 4,727,867 A | 3/1988 | Knoderer |
| 4,755,139 A | 7/1988 | Abbatte et al. |
| 4,763,791 A | 8/1988 | Halverson et al. |
| 4,765,324 A | 8/1988 | Lake, Jr. |
| 4,791,941 A | 12/1988 | Schaefer |
| 4,793,803 A | 12/1988 | Martz |
| 4,799,500 A | 1/1989 | Newbury |
| 4,810,192 A | 3/1989 | Williams |
| 4,838,238 A | 6/1989 | Lee, Jr. |
| 4,848,365 A | 7/1989 | Guarlotti et al. |
| 4,867,147 A | 9/1989 | Davis |
| 4,920,984 A * | 5/1990 | Furumichi .................. 128/861 |
| 4,944,947 A | 7/1990 | Newman |
| 4,955,393 A | 9/1990 | Adell |
| 4,976,618 A | 12/1990 | Anderson |
| 4,977,905 A | 12/1990 | Kittelsen et al. |
| 4,989,616 A | 2/1991 | Lee, Jr. |
| 5,031,611 A | 7/1991 | Moles |
| 5,031,638 A | 7/1991 | Castaldi |
| 5,063,940 A | 11/1991 | Adell et al. |
| 5,076,785 A | 12/1991 | Tsai |
| 5,082,007 A | 1/1992 | Adell |
| 5,103,838 A | 4/1992 | Yousif |
| 5,112,225 A | 5/1992 | Diesso |
| 5,117,816 A | 6/1992 | Shapiro |
| D328,494 S | 8/1992 | Schwendeman et al. |
| 5,152,301 A | 10/1992 | Kittelsen et al. |
| 5,154,609 A | 10/1992 | George |
| 5,165,424 A | 11/1992 | Silverman |
| 5,174,284 A | 12/1992 | Jackson |
| 5,194,003 A | 3/1993 | Garay et al. |
| 5,194,004 A | 3/1993 | Bergersen |
| 5,203,351 A | 4/1993 | Adell |
| 5,234,005 A | 8/1993 | Kittelsen et al. |
| 5,235,991 A | 8/1993 | Minneman |
| 5,259,762 A | 11/1993 | Farrell |
| 5,277,203 A | 1/1994 | Hays |
| D343,928 S | 2/1994 | Kittelsen |
| 5,293,880 A | 3/1994 | Levitt |
| 5,297,960 A | 3/1994 | Burns |
| 5,299,936 A | 4/1994 | Ueno |
| 5,302,117 A | 4/1994 | Kraut et al. |
| 5,313,960 A | 5/1994 | Tosasi |
| 5,316,474 A | 5/1994 | Robertson |
| 5,320,114 A | 6/1994 | Kittelsen et al. |
| 5,323,787 A | 6/1994 | Pratt |
| 5,328,362 A | 7/1994 | Watson et al. |
| 5,336,086 A | 8/1994 | Simmen |
| 5,339,832 A | 8/1994 | Kittelsen et al. |
| 5,353,810 A | 10/1994 | Kittelsen et al. |
| 5,365,946 A | 11/1994 | McMillan |
| 5,385,155 A | 1/1995 | Kittelsen et al. |
| 5,386,821 A | 2/1995 | Poterack |
| D356,188 S | 3/1995 | Kittelsen |
| 5,401,234 A | 3/1995 | Libin |
| 5,406,963 A * | 4/1995 | Adell .................. 128/861 |
| 5,447,168 A | 9/1995 | Bancroft |
| 5,460,527 A | 10/1995 | Kittelsen |
| 5,469,865 A | 11/1995 | Minneman |
| 5,490,520 A | 2/1996 | Schaefer et al. |
| 5,511,562 A | 4/1996 | Hancock |
| 5,513,656 A | 5/1996 | Boyd, Sr. |
| 5,533,524 A | 7/1996 | Minneman |
| D373,421 S | 9/1996 | Brown |
| 5,566,684 A | 10/1996 | Wagner |
| 5,584,687 A * | 12/1996 | Sullivan .................. 433/6 |
| 5,586,562 A | 12/1996 | Matz |
| 5,590,643 A | 1/1997 | Flam |
| 5,592,951 A | 1/1997 | Castagnaro |
| 5,624,257 A | 4/1997 | Farrell |
| 5,636,379 A | 6/1997 | Williams |
| 5,646,216 A | 7/1997 | Watson et al. |
| 5,649,534 A | 7/1997 | Briggs, III |
| 5,666,973 A | 9/1997 | Walter |
| 5,692,523 A | 12/1997 | Croll et al. |
| 5,718,243 A | 2/1998 | Weatherford et al. |
| 5,718,575 A | 2/1998 | Cross, III |
| 5,730,599 A | 3/1998 | Pak |
| 5,746,221 A | 5/1998 | Jones et al. |
| D397,442 S | 8/1998 | Kittelsen |
| 5,816,255 A | 10/1998 | Fishman et al. |
| 5,819,744 A | 10/1998 | Stoyka, Jr. |
| 5,823,193 A | 10/1998 | Singer et al. |
| 5,823,194 A | 10/1998 | Lampert |
| 5,826,581 A | 10/1998 | Yoshida |
| 5,836,761 A | 11/1998 | Belvedere et al. |
| 5,865,619 A | 2/1999 | Cross, III et al. |
| 5,873,365 A | 2/1999 | Brown |
| 5,879,155 A | 3/1999 | Kittelsen |
| 5,915,385 A | 6/1999 | Hakimi |
| 5,921,240 A | 7/1999 | Gall |
| 5,931,164 A | 8/1999 | Kiely et al. |
| 5,947,918 A | 9/1999 | Jones et al. |

| | | |
|---|---|---|
| 5,970,981 A | 10/1999 | Ochel |
| 6,012,919 A | 1/2000 | Cross, III et al. |
| 6,036,487 A | 3/2000 | Westerman |
| 6,039,046 A | 3/2000 | Swartz et al. |
| 6,068,475 A | 5/2000 | Stoyka, Jr. |
| 6,082,363 A | 7/2000 | Washburn |
| 6,092,524 A | 7/2000 | Barnes, Sr. |
| 6,098,627 A | 8/2000 | Kellner et al. |
| 6,109,266 A | 8/2000 | Turchetti |
| 6,257,239 B1 * | 7/2001 | Kittelsen .................... 433/6 |

OTHER PUBLICATIONS

Stephen D. Smith, D.M.D., Muscular Strength Correlated to Jaw Posture and the Temporomandibular Joint, New York State Dental Journal, vol. 44, No. 7, Aug.–Sep. 1978.

W.B. May, D.D.S., Reduction of Stress in the Chewing Mechanism—Part III.

* cited by examiner

DENTAL APPLIANCE WITH ANTIMICROBIAL ADDITIVE

BACKGROUND OF THE INVENTION

This application is a continuation-in-part of U.S. patent application Ser. No. 09/658,102, filed on Sep. 8, 2000 now U.S. Pat. No. 6,257,239 for a Dental Appliance with Antimicrobial Additive.

This invention relates to dental appliances and mouthguards, and more particularly to dental appliances and mouthguards with antimicrobial additives to resist the growth of fungus, yeast, virus, bacteria and the like which may cause illness, infection or gum disease.

It is well known that athletes who are in contact sports wear mouthguards to protect their teeth from sharp blows as well as to protect the head and temporomandibular joint from concussion. Mouthguards are common in football, hockey, soccer, rugby, boxing, for example. Mouthguards may be considered a subgroup of dental appliances.

There is also a trend for athletes, such as body builders, weight lifters, baseball batters, golfers, football players, hockey players, and bowlers to wear dental appliances to prevent the clenching of their teeth during exertion which results in hundreds of pounds of compressed force exerted from the lower jaw onto the upper jaw. Teeth clenching also occurs in bruxing and child birthing. Clenching can result in headaches, muscle spasms, damage to teeth and injury to the temporomandibular joint as well as pain in the jaw. Thus, dental appliances have been created having posterior pads to be positioned between the upper and lower teeth to prevent clenching and damage to one's teeth and jaw structures.

It also is well known that there are dental appliances for a myriad of other uses. Splints, which look like mouthguards, are used for bleaching of teeth, while other appliances may be used to control breathing and snoring. Dentists also use appliances in administering to teeth during dentistry.

It is well known that the mouth and articles that are repeatedly placed into the mouth are subject to the growth of fungus, yeast, virus, and bacteria thereon. One method for treatment to resist such growth includes sterilization. Washing or application of antimicrobial agents is also another method of cleansing appliances.

There is a need for dental appliances of a variety of shapes and uses which resist growth of fungus, yeast, virus and bacteria on the dental appliance as well as on the mouth itself which otherwise may result in gum diseases.

SUMMARY OF THE INVENTION

A dental appliance adapted to lie within the mouth of a person consisting of occlusal posterior pads optionally with a connective arch or a unshaped style base with upstanding labial and/or buccal walls. An antimicrobial additive is incorporated into the resin concentrate prior to molding of the dental appliance which will permit controlled migration from the appliance internal regions to the surface of the appliance.

A principle object and advantage of the present invention is the addition of antimicrobial agents to the appliance to resist the growth of fungus, yeast, virus and bacteria thereon.

Another object and advantage of the present invention is that the antimicrobial agent may be delivered from the appliance directly into the mouth and over the gums to treat and prevent gum diseases.

Another object and advantage of the present invention is that an appliance with the antimicrobial agent will not require sterilization or other extensive cleansing to remove or destroy fungus, yeast, virus and bacteria.

Other objects and advantages will become obvious with the reading of the following specification and appended claims with a review of the figures.

DETAILED DESCRIPTION OF THE PREFERRED EMBODIMENT

The physical structure of dental appliances may be appreciated by reviewing FIGS. 1 through 4.

Figure 1:
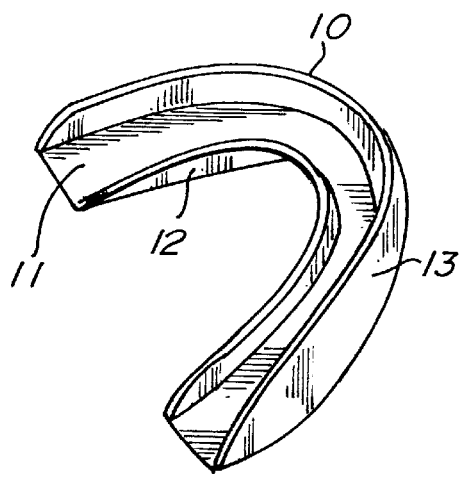
FIG. 1 is a perspective view of a traditional mouthguard suitably made of an elastomer and not designed for custom fit.
Figure 2:
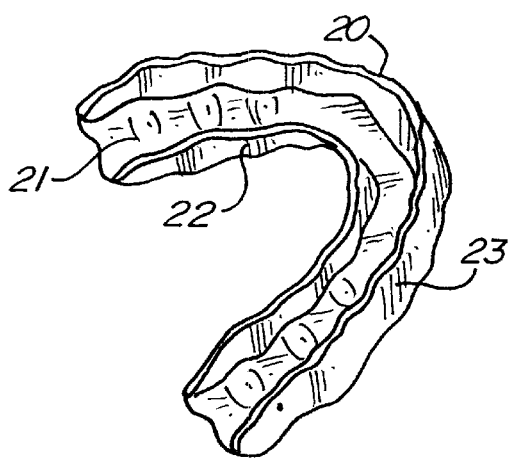
FIG. 2 is a perspective view of a custom fit mouthguard, dental appliance or splint which has been formed to the shape of the teeth and gums.

In FIG. 1, the standard non-custom mouthguard 10 generally includes a horseshoe or u-shaped base or occlusal pad 11 with a lingual wall 12 and a labial wall 13. In FIG. 2, the custom mouthguard or dental appliance 20 may have a base 21, a lingual wall 22, and a labial wall 23. Typically, the custom mouthguard 20 is placed in boiling water to soften, then fitted to the mouth for a sure-grip fit to the wearer.

Figure 3:
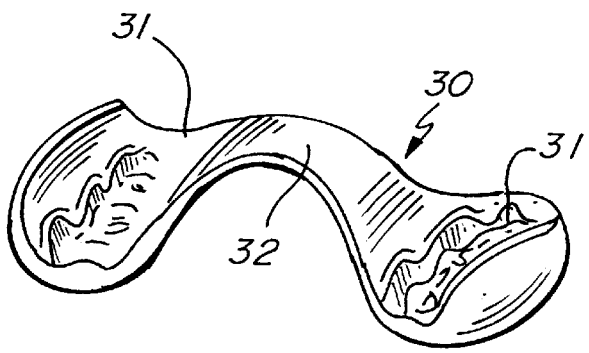
FIG. 3 is a perspective view of a dental appliance with occlusal posterior pads and a connective arch.
Figure 4:
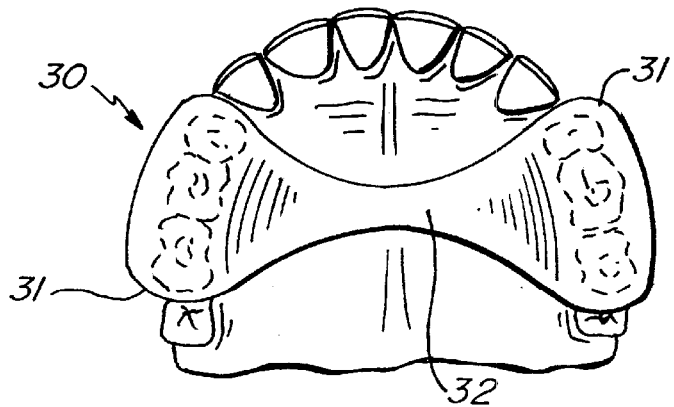
FIG. 4 is a bottom plan view of a dental appliance placed on the upper jaw.

FIGS. 3 and 4 show a typical dental appliance 30 other than a protective mouthguard 10 or 20, the appliance 30 typically includes occlusal posterior pads 31 appropriately connected by an arch 32 to assure that the appliance 30 is not swallowed by the wearer. The arch may also extend along the outside or inside of the anterior teeth.

It is well known that illness, infection, tooth decay and/or periodontal disease is caused by bacteria, fungus, yeast, and virus. These microbials can grow and multiply on dental appliances when the appliances are being stored between uses as well as when the appliance is actually being worn or used.

Antimicrobial substances which are non-toxic and free of heavy metal for resisting the growth of the microbials may include CHLORINATED PHENOL (e.g. 5-CHLORO-2-(2,-4-DICHLOROPHENOXY)PHENOL), POLYHEXAMETHYLENE BIGUANIDE HYDROCHLORIDE (PHMB), DOXYCYCLINE, CHLORHEXIDINE, METRONIDAZOLE, THYMOL, ENCALYPOL and METHYL SALYCILATE . TRICLOSAN® from Siba Giegy of Switzerland is also available.

Dental appliances 10, 20 and 30 are suitably are made of polymers such as polypropylene, styrene, polystyrene, polyethelyne, elastomers, urethane, silicon, polyvinyl chloride and polycarbonates, thermoplastics, ethylene vinyl acetate or polyester resins such as polycaprolactone.

Incorporating the antimicrobial agent into the polymer during the manufacture of the dental appliance 10, 20 or 30 is achieved by incorporating the agent into the synthetic polymeric master batch. The antimicrobial agent is suitably placed into the batch in a concentration as high as 10% which will permit a let-down ratio resulting in the final concentration of the antimicrobial agent and the dental appliance of about 0.005 to about 2% by weight.

By encapsulating the antimicrobial agent into the polymer batch mix, the agents survive molten temperatures approximately or above 350° F. and thus the antimicrobial agent loses none of its biocidal properties in the formation of the dental appliance 10, 20 or 30.

It is to be understood that the foregoing description and specific embodiments are merely illustrative of the best mode of the invention and the principles thereof. Various modifications and additions may be made to the present invention by those skilled in the art without departing from the spirit and scope of this invention which is to be limited only by the scope of the appended claims.

We claim:

1. A dental appliance for a mouth having antimicrobial characteristics, comprising:

an antimicrobial additive in an occlusal pad to be placed on teeth within the mouth.

2. The appliance of claim 1, further comprising upstanding lingual and buccal walls extending upwardly from the pad, the pad being unshaped.

3. The appliance of claim 1, further comprising a second pad.

4. The appliance of claim 3, further comprising a connective arch between the pads.

5. A mouthguard having antimicrobial characteristics, comprising:

a unshaped base with upstanding lingual and buccal walls with an antimicrobial additive therein.

6. A dental appliance for a mouth having antimicrobial characteristics, comprising:

an antimicrobial additive in a pair of occlusal pads to be placed on teeth within the mouth and a connective arch between the pads.

* * * * *